(12) United States Patent
Ollmar et al.

(10) Patent No.: US 12,642,459 B2
(45) Date of Patent: Jun. 2, 2026

(54) IMPLANTABLE GLUCOSE SENSOR

(71) Applicant: D.T.R. Dermal Therapy Research Inc., London (CA)

(72) Inventors: Stig Ollmar, Huddinge (SE); Saul Alejandro Rodriguez Duenas, Järfälla (SE); Ana Rusu, Sollentuna (SE); Ulrik Birgersson, Stockholm (SE); Alejandro Fernandez Schrunder, Stockholm (SE)

(73) Assignee: D.T.R. Dermal Therapy Research Inc., London (CA)

( * ) Notice: Subject to any disclaimer, the term of this patent is extended or adjusted under 35 U.S.C. 154(b) by 328 days.

(21) Appl. No.: 18/276,622

(22) PCT Filed: Feb. 9, 2022

(86) PCT No.: PCT/EP2022/053147
§ 371 (c)(1),
(2) Date: Aug. 9, 2023

(87) PCT Pub. No.: WO2022/171684
PCT Pub. Date: Aug. 18, 2022

(65) Prior Publication Data
US 2024/0130642 A1 Apr. 25, 2024
US 2024/0225488 A9 Jul. 11, 2024

(30) Foreign Application Priority Data
Feb. 11, 2021 (EP) .................................... 21156594

(51) Int. Cl.
*A61B 5/00* (2006.01)
*A61B 5/145* (2006.01)

(52) U.S. Cl.
CPC .......... *A61B 5/14532* (2013.01); *A61B 5/686* (2013.01); *A61B 5/6882* (2013.01);
(Continued)

(58) Field of Classification Search
CPC ... A61B 5/14532; A61B 5/686; A61B 5/6882; A61B 2560/0219; A61B 2562/12; A61B 2562/16; A61B 5/0031; A61B 5/053
See application file for complete search history.

(56) References Cited

U.S. PATENT DOCUMENTS

| 5,970,986 A | 10/1999 | Bolz et al. |
| 2003/0195400 A1 | 10/2003 | Glukhovsky |

(Continued)

FOREIGN PATENT DOCUMENTS

| JP | 2012-118086 A | 6/2012 |
| JP | 2017-506995 A | 3/2017 |

OTHER PUBLICATIONS

International Search Report issued in Int'l Application No. PCT/EP2022/053147, mailed May 24, 2022, 3 pages.

(Continued)

*Primary Examiner* — Scott M. Getzow
(74) *Attorney, Agent, or Firm* — McDonnell Boehnen Hulbert & Berghoff LLP

(57) ABSTRACT

An implantable glucose sensor includes: a housing, two injecting electrodes for injecting current into the tissue, two sensing electrodes for measuring impedance in the tissue, a coil within the housing for powering the sensor via a power source, a circuit board within the housing, the circuit board being electrically connected to the two sensing electrodes and the two injecting electrodes and the coil, and a communication unit for communicating data. The communication unit is connected to the circuit board. The two sensing electrodes and the two injecting electrodes are arranged on an outer surface of a first part of the housing. The outer surface of first part is of a convex shape. The two sensing (Continued)

electrodes and the two injecting electrodes are embedded in the convex shape so that they are flush with the outer surface of the convex shape.

19 Claims, 2 Drawing Sheets

(52) U.S. Cl.
    CPC ... *A61B 2560/0219* (2013.01); *A61B 2562/12* (2013.01); *A61B 2562/16* (2013.01)

(56) References Cited

U.S. PATENT DOCUMENTS

| | | | |
|---|---|---|---|
| 2009/0171420 A1* | 7/2009 | Brown | A61N 1/3787 607/116 |
| 2011/0124992 A1 | 5/2011 | Brauker et al. | |
| 2015/0196224 A1 | 7/2015 | Rusu et al. | |
| 2016/0310048 A1 | 10/2016 | Pang | |

OTHER PUBLICATIONS

Written Opinion issued in Int'l Application No. PCT/EP2022/053147, mailed May 24, 2022, 7 pages.

International Preliminary Report on Patentability issued in Int'l Application No. PCT/EP2022/053147, mailed Apr. 17, 2023, 18 pages.

Office Action issued in Japanese Application No. JP2023-545971, mailed on Oct. 28, 2025, 8 pages.

* cited by examiner

IMPLANTABLE GLUCOSE SENSOR

CROSS REFERENCE TO RELATED APPLICATIONS

This application is a U.S. national phase of International Application No. PCT/EP2022/053147, filed Feb. 9, 2022, which claims priority to European Application 21156594.0, filed Feb. 11, 2021, both of which are incorporated by reference herein in their entirety.

FIELD OF DISCLOSURE

The invention relates to the field of implantable sensors for electrical measurements in the body. In particular the invention relates to implantable glucose sensors that apply four-point measurement for the determination of impedance in the body tissue, which can be muscle tissue.

BACKGROUND

Known sensors for implanting in the body typically contain a printed circuit board, a power source and electrodes or chemical electrodes for determining various parameters in the body. Many known sensors have the aim to detect rejection of an organ after organ transplantation by measuring the trend of the impedance in the transplanted organ. A sign of organ rejection is an increase (trend) in electric impedance in an organ (organ tissue) in a transplanted organ. Once such an increase started, a doctor can apply drugs to a certain extent, but if a threshold is reached then the organ will be rejected and basically die within the recipient body. Such a sensor is for instance illustrated in the U.S. Pat. No. 5,970,986 B1.

In the U.S. Pat. No. 5,970,986 B1 an apparatus for rejection diagnostics after organ transplantations, which is equipped with an extra corporal base station comprising a high frequency transmitter and receiver unit that can transmit data to an implantable rejection sensor, is disclosed. The implantable rejection sensor comprises an integrated circuit component, thus an IC component, to which a receiving- and transmitting coil are allocated. The implantable rejection sensor further comprises a sensor arrangement comprising of four electrodes arranged on the plane surface of the housing. U.S. Pat. No. 5,970,986 B1 further states that the electrodes and the coils can be integrated in the IC component. The implantable rejection sensor is configured to be fixed onto a donor organ.

It is herewith important to note that the sensor disclosed in U.S. Pat. No. 5,970,986 B1 is for measuring organ rejection and when doing so the parameter that matters is the trend of the impedance in the organ as explained above. The absolute values of impedance are not critical when detecting organ rejection.

In contrast when glucose concentration is determined in the tissue of an animal or human, which can be summarized with the term living beings, the absolute impedance values are of interest since they are correlated to glucose concentration. If these measured values are false then the correlated glucose values are false, which can lead to unwanted consequences.

One issue that falsifies the measured impedance once a sensor is implanted in the body of a living being is body liquid that collects around certain areas around the implanted sensor and around the electrodes. This body liquid can be blood, wound liquid or other extra cellular liquids or a mixture thereof. Since the electric conductivity is better in liquids, these body liquids affect and falsify the measured impedance and therefore affects the accuracy of the measurement. Tests and reference measurements have shown that body liquids affect the accuracy of the impedance measurements substantially.

The sensor shown in the U.S. Pat. No. 5,970,986 B1 has exactly this problem due its sharp edges and flat surfaces. However, since U.S. Pat. No. 5,970,986 B1 is concerned with detecting organ rejection, this problem is not mentioned in the document.

Another problem of many known sensors is that the coil for receiving the magnetic field from a power source for powering the sensor is arranged on, under or above the printed circuit board (PCB) of the sensor. Since the PCB typically contains conducting loops and the like, the magnetic field induces Eddy Currents in the PCB, which Eddy Currents can affect the measurement performance and disturb the energy or power transfer from the power source to the sensor by reducing the allowable or workable distance between the implanted sensor and the external reader.

SUMMARY

It is therefore an object of the present invention to provide an improved sensor for determining glucose so that the impedance measurement within tissue of a living being where the glucose sensor is implanted is exact.

It is another object of the invention to provide a glucose sensor that is reliable and safe.

It is a further object of the invention to provide a glucose sensor that is easy to handle for a patient.

In view of the above-mentioned problems and objects the inventors of the present invention have discovered that the outer shape of the housing and the shape of the electrodes for determining impedance in the tissue should be adjusted when glucose sensors are designed. The inventors have further discovered that any sharp edges of flat surfaces should be avoided for an optimal result. They also discovered that Eddy Currents induced via the pulsed magnetic field can be minimized by arranging the coil geo-metrically separated from the circuit board or circuitry and the injecting and sensing electrodes for improved measurement performance and when using a mobile device to power the sensor via the coil.

It is further to be noted that the inventors of the present invention have found that the accumulation or movements of body liquids in the vicinity of the implantable glucose sensor will influence the results significantly, particularly in the immediate vicinity of the sensing pair of electrodes. This was shown in model calculations. The model calculations also showed that, in particular the sensing electrodes, should be perfectly flush with the outer surface of the housing and the outer surface of the first part, respectively, of the implantable glucose sensor. This led to the discovery that the housing of the implantable glucose sensor should be convex, convex on all sides, egg shaped, ellipsoidal or super-ellipsoidal in order to stretch the tissue around the implantable glucose sensor for preventing the formation of body liquid pockets in the immediate vicinity of the implantable glucose sensor. The presence of such body liquid filled pockets can also be caused by either movement of the patient, physical impacts from an external source or pressure from an external source to the body of the patient. All of these artefacts are eliminated by the herein disclosed shape proposals of the implantable glucose sensor.

Disclosed herein is an implantable glucose sensor for determining impedance in tissue of a living being. The implantable glucose sensor comprises:

a housing, two injecting electrodes for injecting current into the tissue, two sensing electrodes measuring impedance in the tissue, whereby the two sensing electrodes are separate from the two injecting electrodes, a coil arranged within the housing for powering the implantable glucose sensor via a power source, a circuit board arranged within the housing, the circuit board being electrically connected to the two sensing electrodes and the two injecting electrodes and the coil, a communication unit for transferring and receiving data packages, the communication unit being connected to the circuit board, the housing comprising at least a first part and a second part, the two sensing electrodes and the two injecting electrodes being arranged on an outer surface of the first part.

The outer surface of first part is of convex shape and the electrodes are embedded in the convex shape so that they are flush with the outer surface of the convex shape, the coil being geometrically separated from the injecting electrodes, the sensing electrodes and the circuit board within the housing.

The geometrical separation of the coil from the other electric components and the sensing electrodes, the injecting electrodes and the circuit board or circuitry substantially reduces Eddy Currents in these components when the implantable glucose sensor is powered via the coil by an external device. Such Eddy Currents absorb the energy that is transferred to the coil via the external device, which means that the energy that is transferred from the pulsed magnetic field generated by the external device is reduced and for example converted into heat. The heat in itself is not a problem, a problem is that the energy that is now received by the coil will not be enough to power measurement of the impedance and the communication between the sensor and the external device. The small coil inside the sensor and the large coil in the outside reader device should be aligned.

In case the housing is shaped as an ellipsoid or egg shape, it will always define a longitudinal direction since an ellipsoid or flattened egg shape is always longer in one direction than in the two other directions. The ellipsoid (or egg shape) can be split in half along a plane that is perpendicular to the longitudinal direction and which plane is extending through the centre of the ellipsoid or egg. One of these two halves, a first half comprises the coil while the second half comprises the injecting electrodes and the sensing electrodes on the outer surface of the ellipsoid and the circuit board. The second half may further comprise the communication unit.

Independently if the sensor or the housing is convex shaped, double convex shaped, egg shaped, ellipsoid shaped or super ellipsoid shaped it is to be noted that the sensor or the housing has an elongated shape. An elongated shape means that one axis extending through the sensor can be identified as a longitudinal axis.

The above construction and separation of the coil from the other electronic components in particular the sensing electrodes, the injecting electrodes and the circuit board, leads to the strong reduction of Eddy Currents when the implantable glucose sensor is powered during measurement via the external device.

The avoidance or at least the reduction of Eddy Currents is important since the implantable glucose sensor will only perform glucose measurements when it is powered via an external device with pulsed magnetic field to the implanted glucose sensor. The external device can thereby induce electric current in the circuit board, the sensing and injecting electrodes or the electrical connection between these, since the external device powers the implanted sensor via the coil of the implanted sensor and the pulsed magnetic field originating from the external device, which pulsed magnetic field can induce currents within conductors (Eddy Currents). That is the reason why Eddy Currents in the circuit board and the sensing and injecting electrodes and the communication module need to be prevented, since they directly affect the measurement of the impedance by eating up energy of the pulsed magnetic field, which energy is then not available to perform the tasks in the sensor. Physically separating the circuit board and the coil within the sensor housing not allowing an overlap between the circuit board and the coil. This offers the best effect to avoid Eddy Currents, which will result in reduced energy transfer.

The coil and the circuit board must be displaced sideways or neighbouring one another. They may be arranged next to one another without any overlap. The circuit board and the coil are not overlapping but arranged next to one another in a direction seen perpendicular to the longitudinal axis.

The external device may be a mobile phone or the like.

The outer surface of the implantable glucose sensor is as smooth as possible, for instance in a range of ISO grade numbers N1 to N5, Roughness Ra values of between 0.025 to 0.4 micrometers.

The outer skin of the implantable glucose sensor and the housing, respectively, may be made of silicone. Alternatively, the entire housing may be made of silicone.

The sensing electrodes and the injecting electrodes may be fully integrated in the silicone.

Having a surface that is as smooth as possible without any sharp edges scratches or the like on the surface, ensures that no liquid accumulation occurs around the outer surface of the sensor when it is implanted. The occurrence of liquids, liquid pockets around the outer surface of the sensor, which liquids or liquid pockets are in direct contact with the outer surface can affect and falsify the measurement and need to be avoided.

This can be achieved by designing a very smooth and harmonic outer surface or housing of the sensor.

The above explained avoidance of liquids extends to the integration of the sensing and injecting electrodes into the outer skin of the sensor or housing. They must be perfectly flush and integrated in the outer surface of the sensor and housing for avoiding the accumulation of (body) liquids.

The outer surface of the sensor or housing and the outer surface of the sensing and injecting electrodes may be polished in order to achieve the highest possible smoothness.

The convex shape of the outer surface prohibits the formation of body liquid around the implanted glucose sensor and in particular around the electrodes and therefore improves the accuracy of the measured impedance values of the tissue, which again improves the glucose concentration correlation.

It is to be noted that the second part of the housing does not need to be of convex shape, it may be designed as a plane and therefore flat.

Even though the production of such convexly shaped housings for implantable glucose sensors is not cheap, the long term benefits in measuring accuracy outweigh this cost.

Fastening means, such as small loops or hooks, are arranged on the second part of the housing and allow the fastening of the implantable glucose sensor within a living being.

Arranging the fastening means on the second part reduces the influence of the fastening in the measurement process. The actual fastening of the implantable glucose sensor on tissue can create scar tissue, which can affect the measurement accuracy. In case body liquid accumulates around the fastening means after surgery and implanting, respectively, the measurement at the two sensing electrodes and the two injecting electrodes is not affected.

In an embodiment, the coil is arranged next to the circuit board.

This reduces the effects of Eddy Currents on the circuit board when a power source is used to power the implantable glucose sensor via a magnetic field.

In another embodiment the housing is shaped harmonic and rounded off.

A rounded shaped housing that is also harmonically shaped, reduces the risk of accumulation of body liquids.

In one embodiment two injecting electrodes may have a longitudinal shape, such as for example an elliptic longitudinal shape or a rectangular longitudinal shape.

A longitudinal shape of the current injecting electrodes improves the electric field that is generated and therefore the measurement by the two measuring electrodes is improved.

For further improved measuring performance the two measuring electrodes may be arranged in between the injecting electrodes.

In another embodiment the housing may be of an ellipsoidal or super ellipsoidal shape.

An ellipsoid shape, ellipsoidal shape, super-ellipsoid- or super-ellipsoidal shape can further prohibit the formation of body liquid around the implantable glucose sensor.

In one embodiment the two injecting electrodes and the two measuring electrodes may be integrated in the first part of the housing, for example during injection moulding.

The implantable glucose sensor may be made of a biocompatible material and the electrodes may be made of gold or other biocompatible and conductive material.

The implantable glucose sensor may have a length of 10 mm to 50 mm, preferably 20 mm to 30 mm, a width of 5 mm to 25 mm, preferably 11 mm to 15 mm and a thickness of 1 mm to 15 mm, preferably 2 mm to 5 mm.

Explanation of Terms

Below certain expressions and terms used herein are explained and defined.
Harmonic and/or Rounded Off This expression herein describes a sensor housing that is rounded and generally harmonic shaped. A harmonic and rounded off housing does not comprise any edges or corners and in particular no sharp edges and sharp corners. The expression harmonic and rounded off herein also includes and covers an ellipsoid shape, a double convex shape, an egg shape, any ellipsoidal like shape, super ellipsoidal-like shapes and spheric shapes and any hybrid in between ellipsoid and spheric or egg. The term harmonic and/or rounded off also includes a super ellipsoid shape.
Convex and/or Convexly Shaped The terms convex and/or convexly shaped herein refer to a shape that is bellying out towards an outer side, in the present case towards the body tissue, which is the outer side, when the implantable glucose sensor is implanted. The first part of the housing is thus extending away from the inside of the housing and thus away from the circuit board, the coil and the communication unit in that it is bulging away from it. The convex or convexly shape of the first part can be polygonal or totally rounded and smooth. While polygonal is not optimal it improves measurement accuracy compared to square shaped sensors and therefore flat surfaces.

The embodiments illustrated herein can be combined and various features of one embodiment can be introduced in other embodiments. The features illustrated in one embodiment may be applied in another embodiment. None of the features are in particular excluded from being employed or implemented in another embodiment shown herein.

BRIEF DESCRIPTION OF THE DRAWINGS

The present invention will now be described, for exemplary purposes, in more detail by way of an embodiment(s) and with reference to the enclosed drawings, in which.

DETAILED DESCRIPTION

Figure 1:
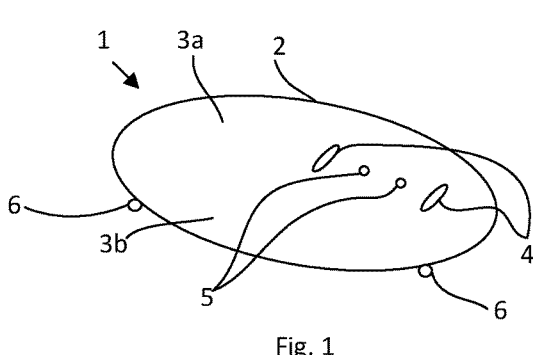
FIG. 1 schematically illustrates a perspective view of an ellipsoidal implantable glucose sensor.

FIG. 1 illustrates an implantable glucose sensor 1 comprising a housing 2 of double convex, ellipsoidal or ellipsoidal shape, the housing comprising a first part 3a and a second part 3b. The first part 3a, which could be considered the upper first part 3a, comprises two injecting electrodes 4 and two sensing electrodes 5. The injecting electrodes 4 are configured to inject current and the sensing electrodes 5 are configured to measure and determine impedance. The second part 3b, which could be considered the lower second part 3b, comprises fastening means 6 for fastening the implantable glucose sensor 1 to tissue. The fastening means 6 can be employed in the form of loops or hooks. In FIG. 1 loops are shown. Please note that these fastening means 6 are only shown in the embodiment according to FIG. 1, these fastening means 6 can however be employed in any other embodiment, preferably on the second part 3b of the housing 1. The injecting electrodes 4 and sensing electrodes 5 are integrated in the housing 1 and arranged smooth and flush with an outer surface of the first part 3a. The injecting electrodes 4 are of a longitudinal shape whereas the sensing electrodes 5 are shown circular. In the illustrated example in FIG. 1 the housing 2 has a double convex, an ellipsoidal or ellipsoidal shape.

Figure 2:
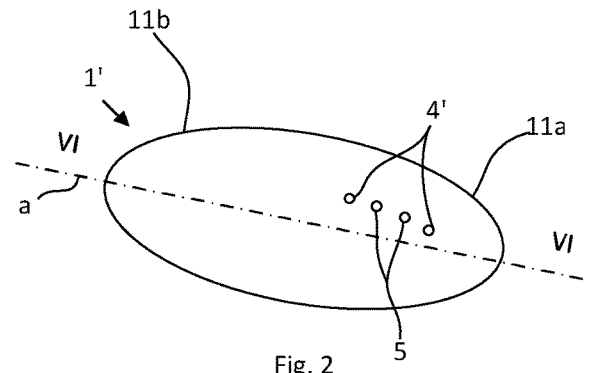
FIG. 2 schematically illustrates a perspective view of an embodiment similar as the one shown in FIG. 1.

FIG. 2 illustrates a similar embodiment of an implantable glucose sensor 1' as FIG. 1 but in this case with circular injecting electrodes 4'. All other features are the same or similar to the embodiment shown in FIG. 1. The fastening means are however not illustrated.

In the embodiments shown in FIGS. 1 and 2, the injecting and sensing electrodes 4, 4', 5 are arranged in a row on the outer surface of the first part 3a with the two sensing electrodes 5 being arranged in between the two injecting electrodes 4, 4'.

FIG. 2 further illustrates the longitudinal axis a of the housing 2. In addition, FIG. 2 also illustrates the first half 11a and the second half 11b of the housing. The first half 11a and the second half 11b being defined by splitting the housing 2 in the middle as seen along the longitudinal axis a or split by a plane that extends perpendicular to the longitudinal axis a and that extends through a center of the housing 2.

Figure 3:
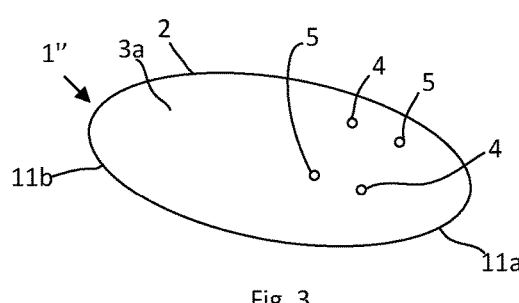
FIG. 3 schematically illustrates a perspective view of an embodiment similar as the one shown in FIG. 1.

Turning now to FIG. 3, which still shows another embodiment of the implantable glucose sensor 1" whereby the two injecting electrodes 4 and the two sensing electrodes 5 are arranged on the outer surface of the first part 3a of the housing 2 defining a rectangular shape. The injecting and sensing electrodes 4, 5 are thus arranged on the corners of a imaginary rectangle or quadrat. All other features are the same or similar to the embodiment shown in FIGS. 1 and 2. The fastening means are however not illustrated.

Also in FIG. 3 the first half 11a and the second half 11b is well illustrated.

Figure 4:
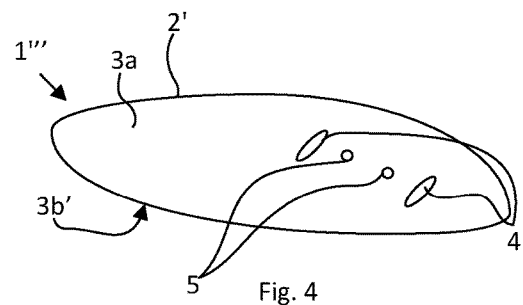
FIG. 4 schematically illustrates a perspective view of another embodiment of the implantable glucose sensor.

FIG. 4 illustrates a further embodiment of the implantable glucose sensor 1''' whereby the housing 2' comprises the first part 3a with the injecting electrodes 4 and the sensing electrodes 5, similar to the ones illustrates in the embodiment of FIG. 1. The second part 3b' of the housing 2 is formed flat and as a plane. The first part 3a is still convexly shaped. The transformation from the first part 3a to the second part 3b' may preferably be rounded off and not formed as sharp edge.

Figure 5:
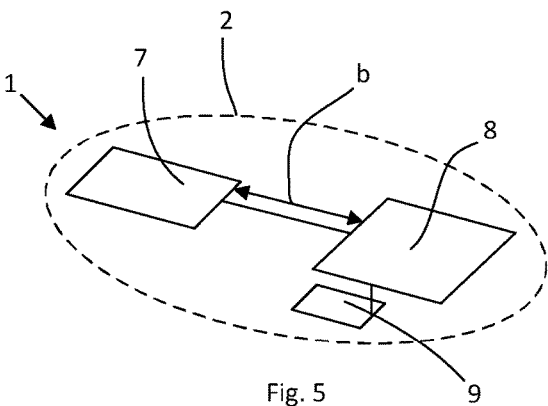
FIG. 5 schematically illustrates the interior of an implantable glucose sensor with certain parts omitted for illustrative purposes.

FIG. 5 illustrates the interior of the implantable glucose sensor 1, 1', 1", 1''' and illustrates a coil 7, a circuit board 8 and a communication unit 9, which are electrically connected to one another. The housing 2 is shown in dashed lines to illustrate that is omitted for illustrative purposes. The coil 7 is arranged next to the circuit board 8 but not overlapping. As can be seen from FIG. 5, the two injecting electrodes 4, 4' and the two sensing electrodes 5 are arranged on the side of the housing 2 that is arranged around the circuit board 8. The two injecting electrodes 4, 4' and the two sensing electrodes 5 are thus arranged above the circuit board 8 and not above the coil 7.

In FIG. 5 the distance b is further shown, which distance b is a distance between the circuit board 8 and the coil 7 as measured along the longitudinal direction a (c.f. FIG. 2).

Figure 6:
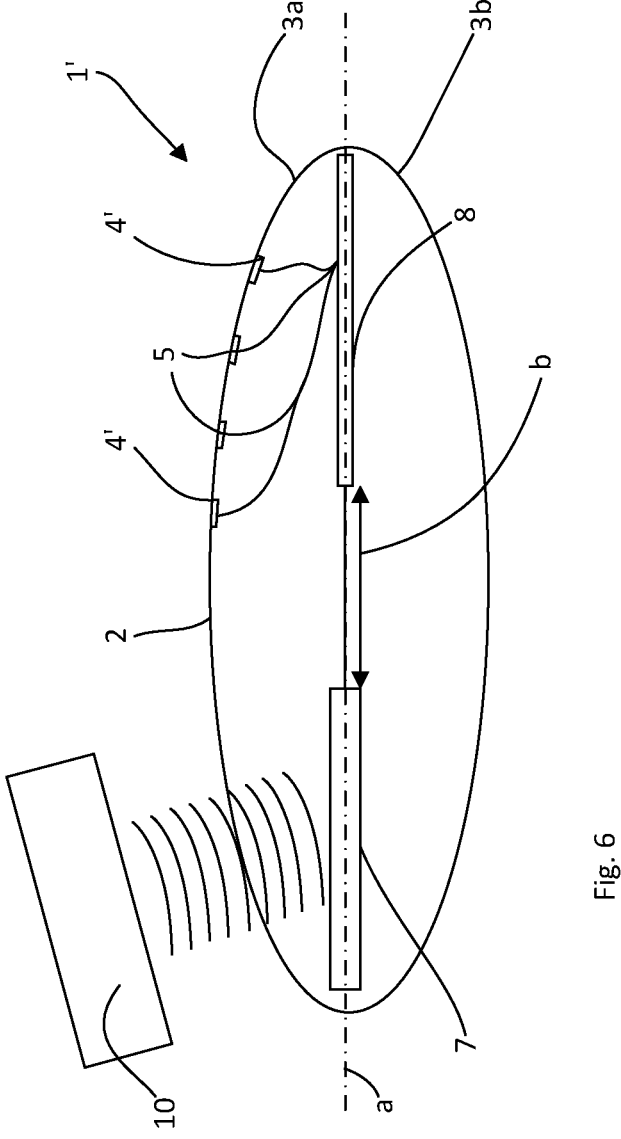
FIG. 6 schematically illustrates a cross sectional view of the implantable glucose sensor along line VI-VI of FIG. 2.

As explained above, the spacing of the coil 7 away from the circuit board 8 by the distance b reduces the presence of Eddy Currents when the implantable glucose sensor 1, 1', 1", 1''' is powered by an external power source 10 as illustrated in FIG. 6.

FIG. 6 illustrates a cross sectional view through the implantable glucose sensor 1' of FIG. 2. The coil 7, the circuit board 8 and the communication unit 10 are illustrated and it is also illustrated how the external power source 10, which can for instance be any type of reading device or a smartphone, is powering the coil via a pulsed magnetic field. The current injecting electrodes 4' and the current sensing or current measuring electrodes 5 are also illustrated including their electric connection to the circuit board 8. The housing 2 comprising the first part 3a, with the two injecting electrodes 4' and the two sensing electrodes 5, is well visible and also the feature that all the electrodes are arranged above the circuit board 8 and not around or above the coil 7. This avoids unwanted electric and/or electromagnetic effects such as Eddy Currents on the two injecting electrodes 4' and the two sensing electrodes 5, during measuring of the tissue impedance.

During the powering of the sensor 1' the communication unit 9 may communicate with the external power source 10 and provide measurement data via wireless communication.

The invention has now been described according to several embodiments and it is herewith to be noted that any combination of the embodiments and shown features is possible in line with the disclosure herein. Various features or amendments can be done in all of the shown embodiments.

The invention claimed is:

1. An implantable glucose sensor configured for determining an impedance in a tissue of a living being, the implantable glucose sensor comprising:
a housing,
two injecting electrodes configured for injecting current into the tissue,
two sensing electrodes configured for measuring the impedance in the tissue, whereby the two sensing electrodes are arranged separately from the two injecting electrodes,
a coil arranged within the housing configured for powering the implantable glucose sensor via a power source,
a circuit board arranged within the housing, the circuit board being electrically connected to the two sensing electrodes, the two injecting electrodes, and the coil,
a communication unit configured for transferring and receiving data packages, the communication unit being connected to the circuit board,
the housing comprising the two sensing electrodes and the two injecting electrodes on an outer surface of the housing, wherein the housing has a shape that is elongated along a longitudinal axis,
wherein the outer surface of the housing is of a convex shape and the two sensing electrodes and the two injecting electrodes are embedded in the convex shape so that they are flush with the outer surface of the convex shape, characterized in that the coil is spaced apart from the circuit board along the longitudinal axis, and spaced apart from the injecting electrodes, the sensing electrodes, and the circuit board within the housing.

2. The implantable glucose sensor according to claim 1, wherein a distance as measured along the longitudinal axis between the circuit board and the coil is chosen so that the circuit board and the coil are not overlapping in a second direction seen perpendicular to the longitudinal axis.

3. The implantable glucose sensor according to claim 1, wherein the housing is shaped harmonic and rounded off.

4. The implantable glucose sensor according to claim 1, wherein the two injecting electrodes have a longitudinal shape.

5. The implantable glucose sensor according to claim 1, wherein the two sensing electrodes are arranged in between the injecting electrodes.

6. The implantable glucose sensor according to claim 1, wherein the housing is of an ellipsoid shape or an egg shape.

7. The implantable glucose sensor according to claim 6, wherein the ellipsoidal shape or the egg shape of the housing defines the longitudinal axis and wherein the ellipsoidal shape comprises at least the sensing electrodes, the injecting electrodes and the circuit board in a first half and wherein the coil is arranged in a second half, the first half and the second half not overlapping the first half as seen in a second direction perpendicular to the longitudinal axis, said second half being defined by a split of the ellipsoidal shape or the egg shape of the housing along a plane that is oriented perpendicular to the longitudinal axis direction and which plane extends through a center of the ellipsoidal shape or the egg shape of the housing.

8. The implantable glucose sensor according to claim 7, wherein the communication unit is also arranged in the first half.

9. The implantable glucose sensor according to claim 1, wherein the housing is of an egg shape.

10. The implantable glucose sensor according to claim 1, wherein the two injecting electrodes and the two sensing electrodes are integrated in the housing, in an injection moulding process.

11. The implantable glucose sensor according to claim 1, wherein the housing is made of a biocompatible material, and wherein the two injecting electrodes and the two sensing electrodes are made of gold or another biocompatible and conductive material.

12. The implantable glucose sensor according to claim 1, wherein the implantable glucose sensor comprises fastening means for fastening the implantable glucose sensor to the tissue of the living being, once it is implanted.

13. The implantable glucose sensor according to claim 1, wherein outer dimensions of the implantable glucose sensor correspond to a length of 10 mm to 50 mm, a width of 5 mm to 25 mm, and a thickness of 1 mm to 15 mm.

14. The implantable glucose sensor according to claim 1, wherein outer dimensions of the implantable glucose sensor correspond to a length of 20 mm to 30 mm, a width of 11 mm to 15 mm, and a thickness of 2 mm to 5 mm.

15. The implantable glucose sensor according to claim 1, wherein the two injecting electrodes have an elliptic longitudinal shape.

16. The implantable glucose sensor according to claim 1, wherein the two injecting electrodes have a rectangular longitudinal shape.

17. The implantable glucose sensor according to claim 1, wherein the housing is made of silicone.

18. The implantable glucose sensor according to claim 1, wherein the outer surface of the housing is convex on all sides of the housing.

19. The implantable glucose sensor according to claim 1, wherein the housing has a first end on the longitudinal axis and a second end opposite the first end on the longitudinal axis, wherein the coil is closer to the first end than the second end, and wherein the injecting electrodes, the sensing electrodes, and the circuit board are closer to the second end than the first end.

* * * * *